United States Patent
Gemma et al.

[11] Patent Number: 6,016,905
[45] Date of Patent: Jan. 25, 2000

[54] SURGICAL SUTURE RETAINER PACKAGE

[75] Inventors: Edward A. Gemma, Milford; Walter Kendrioski, Guilford, both of Conn.

[73] Assignee: United States Surgical Corporation, Norwalk, Conn.

[21] Appl. No.: 09/260,095

[22] Filed: Mar. 2, 1999

Related U.S. Application Data

[60] Provisional application No. 60/077,294, Mar. 6, 1998.

[51] Int. Cl.$^7$ .................................................. A61B 17/06
[52] U.S. Cl. .......................................... 206/63.3; 206/380
[58] Field of Search .................... 206/63.3, 227, 206/380, 382, 388

[56] References Cited

U.S. PATENT DOCUMENTS

| | | | |
|---|---|---|---|
| 3,648,949 | 3/1972 | Berger et al. ........................... | 242/159 |
| 3,749,238 | 7/1973 | Taylor .................................... | 206/63.3 |
| 4,699,271 | 10/1987 | Lincoln et al. ........................ | 206/63.3 |
| 5,249,673 | 10/1993 | Sinn ...................................... | 206/63.3 |
| 5,335,783 | 8/1994 | Sinn ...................................... | 206/380 |
| 5,814,069 | 9/1998 | Schulze et al. ........................ | 206/63.3 |

*Primary Examiner*—David T. Fidei

[57] ABSTRACT

A package for retaining a needle-suture combination includes a cover, and a base which is connected to the cover by snap lock engagement so as to define an enclosure volume. The base has first and second V-shaped ridges, each V-shaped ridge having a vertex portion, the vertex portion of the first V-shaped ridge being in opposing relation to the vertex portion of the second V-shaped ridge so as to define a constricted space therebetween. The V-shaped ridges serve as guides for maintaining a major portion of the suture in a coiled configuration with generally figure 8 shaped loops.

20 Claims, 5 Drawing Sheets

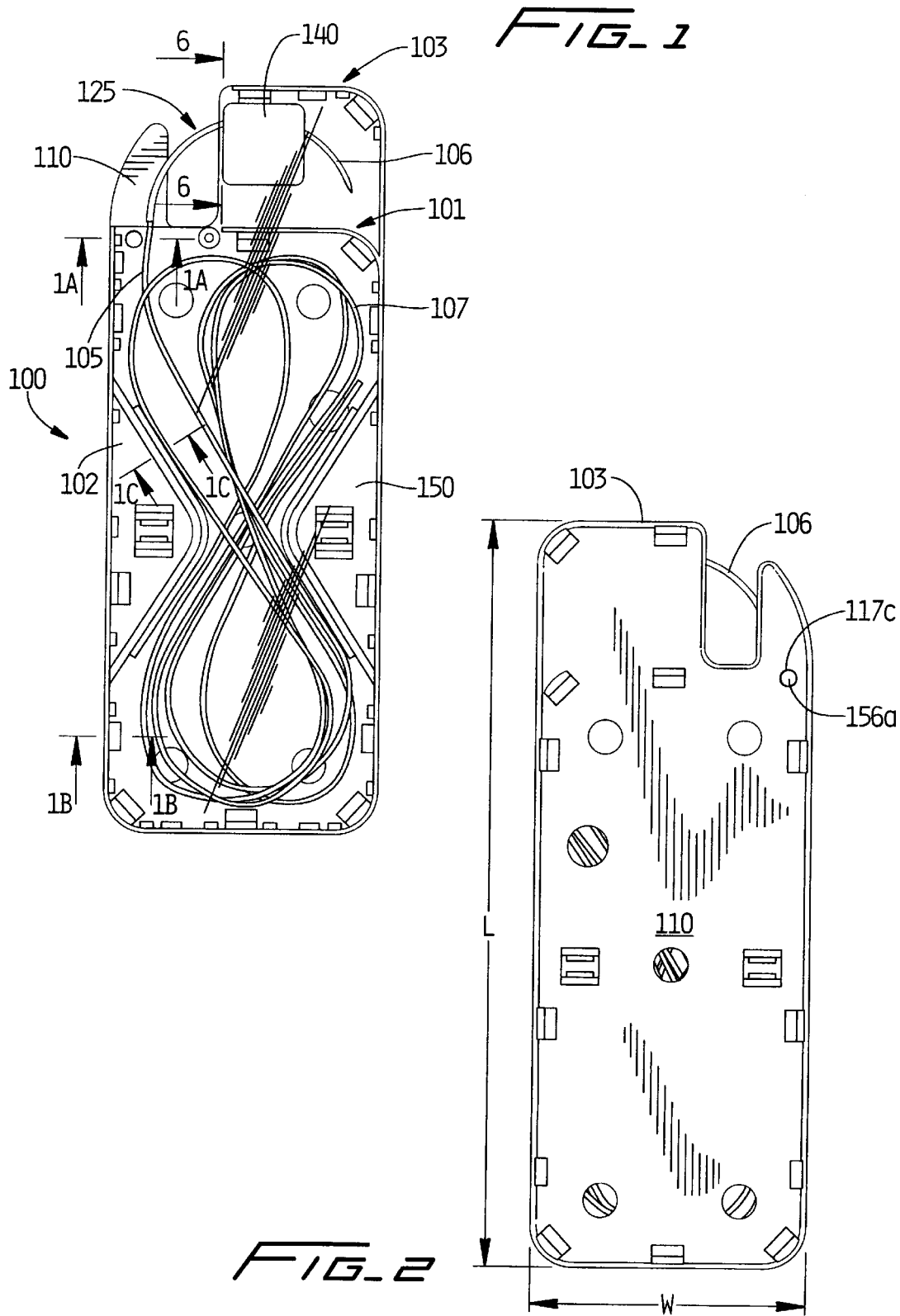

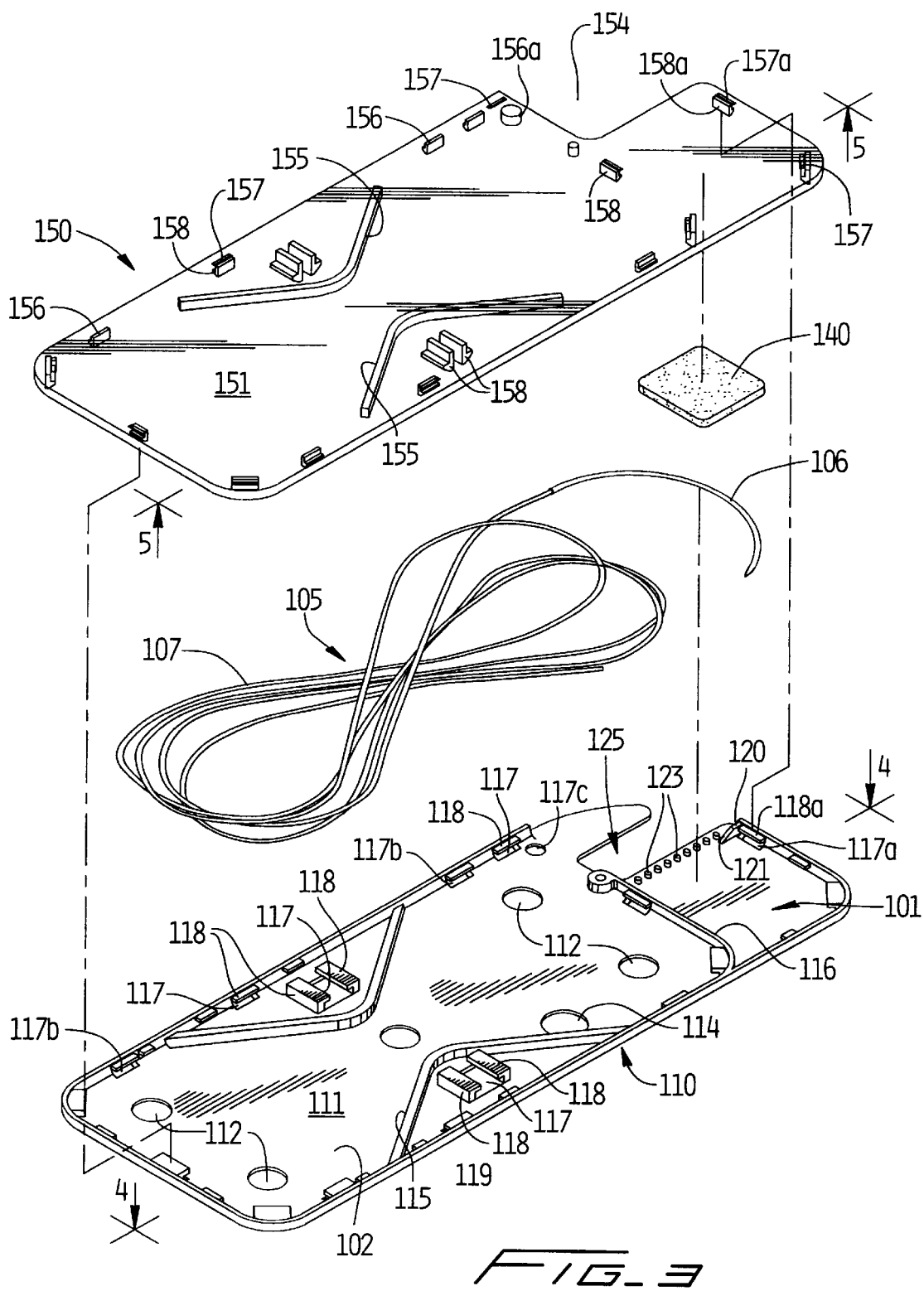

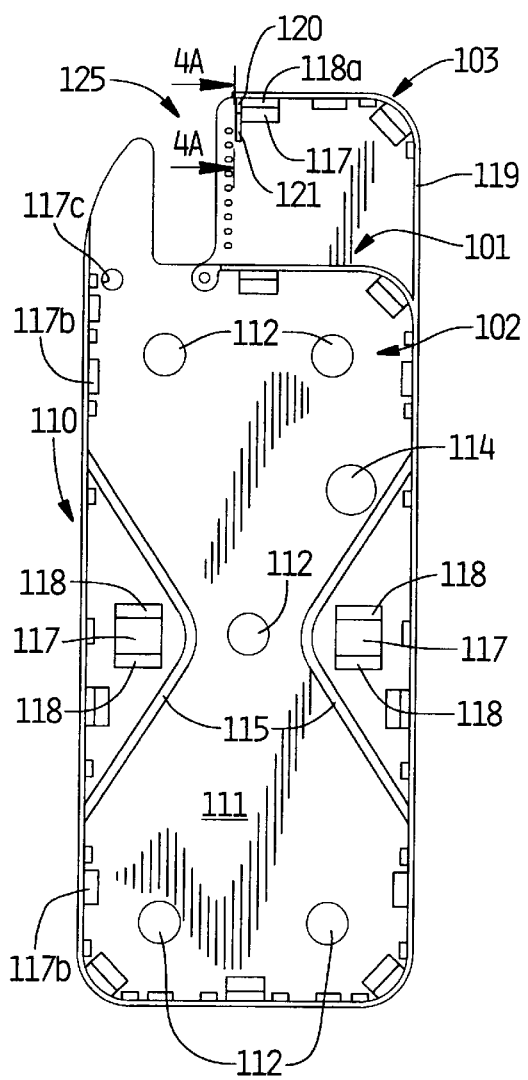
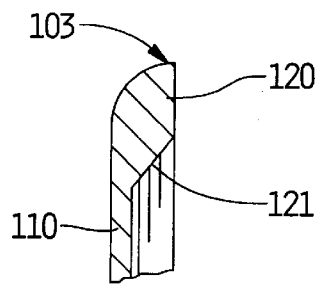
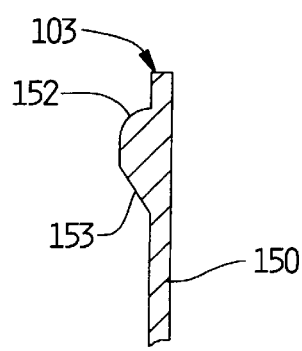
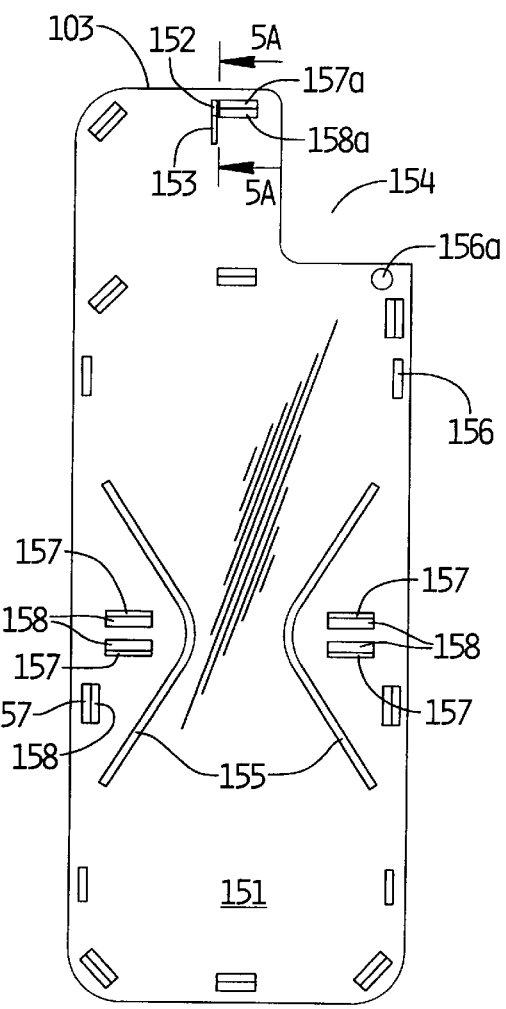

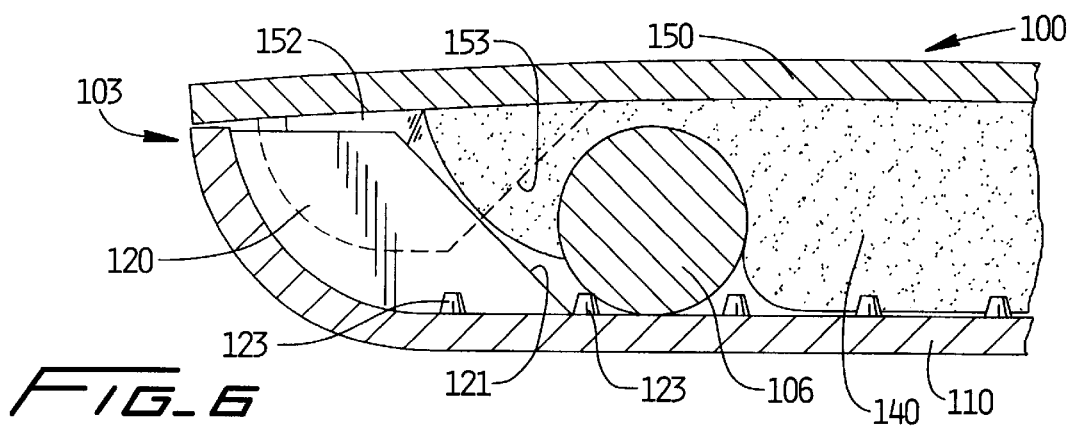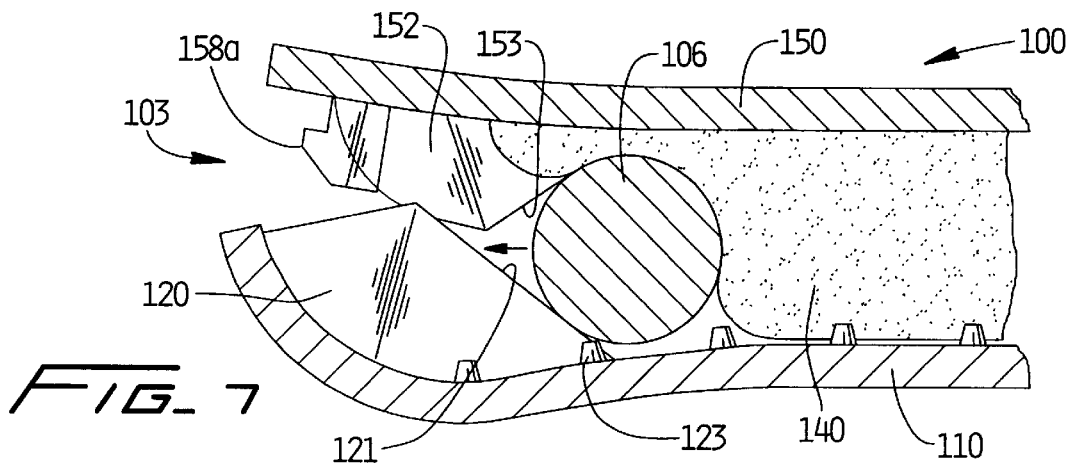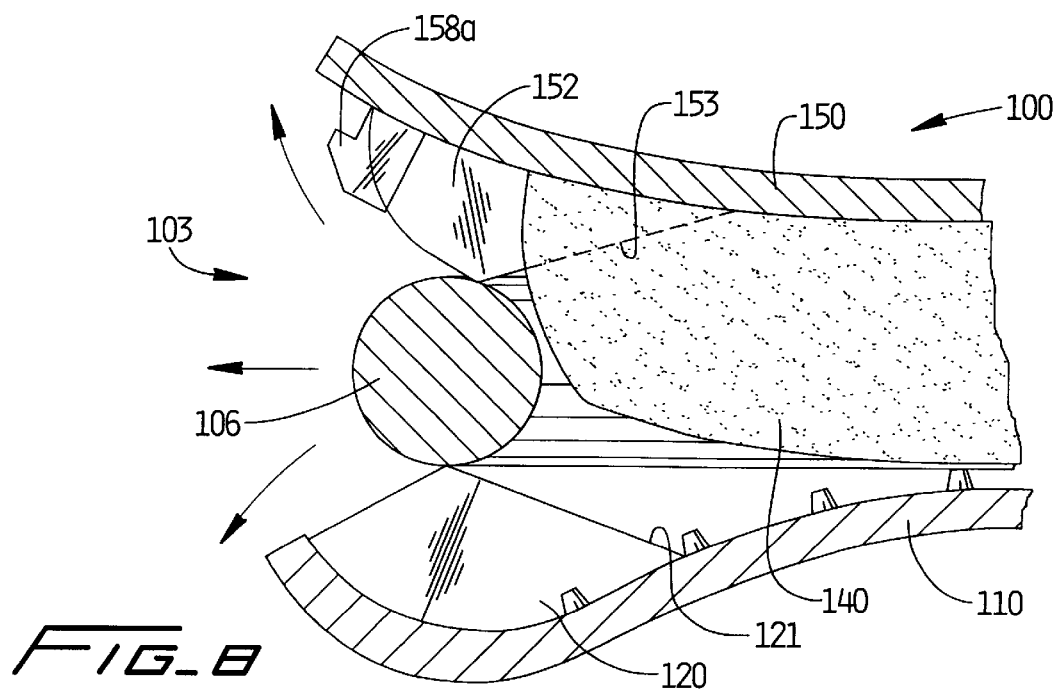

SURGICAL SUTURE RETAINER PACKAGE

This application claims priority from Provisional Application No. 60/077,294, filed Mar. 6, 1998.

BACKGROUND

1. Technical Field

The present disclosure relates to a package for retaining, storing, and dispensing a surgical needle-suture combination.

2. Background of Related Art

Packages for retaining armed sutures, i.e., sutures with surgical needles attached, are known. For example, U.S. Pat. No. 5,566,821 to Brown et al. discloses a surgical suture retainer which retains the suture in an epitrochoidal, or hourglass configuration. One embodiment includes an insert member mounted to one of several foldable connected panels of the suture retainer. The insert member preferably has first and second wings which fold over to form a suture retaining pocket. The suture is held in a looped configuration having an hourglass shape. Another embodiment employs tabs cut from one of the panels to retain the suture in the hourglass shape. Yet another embodiment employs a cover sheet bonded to a base panel, wherein bonding areas are located to maintain the suture loop in an hourglass shape.

U.S. Pat. No. 5,439,102 to Brown et al. discloses a moisture impervious package for surgical elements such as retainers having suture-needle assemblies positioned thereon. The package is provided with a top wall of moisture impervious material having an access opening die cut into the wall over which a closure flap secured by a peripheral heat seal to fully enclose the access opening. The top wall is then positioned over a bottom wall of moisture impervious material whereby a retainer having the suture needle assemblies is positioned therebetween. A peripheral heat seal then secures the top wall to the bottom wall to form the package.

U.S. Pat. No. 5,359,831 to Brown et al. discloses a molded suture retainer for retaining and storing surgical sutures in a manner which reduces kinking and bending of the sutures. The retainer is characterized by a wide spiraling oval passageway with minimal convolutions covered by a cover sheet. The length of the passageway is preferably proportional to ⅓ to ½ the overall length of the suture to be retained therein. Recesses are provided for receiving package stabilizing agents and/or needle parks.

SUMMARY

A package is provided herein for retaining a needle-suture combination. The package comprises a cover, and a base which is connected to the cover by snap lock engagement so as to define an enclosure volume, the base having first and second V-shaped ridges, each V-shaped ridge having a vertex portion, the vertex portion of the first V-shaped ridge being in opposing relation to the vertex portion of the second V-shaped ridge so as to define a constricted space therebetween. The V-shaped ridges serve as guides for maintaining a major portion of the suture in a coiled configuration with generally FIG. 8 shaped loops.

BRIEF DESCRIPTION OF THE DRAWINGS

Various embodiments are described below with reference to the drawings wherein:

FIG. 1 is a top plan view of the suture retainer package with an armed suture stored therein;

FIG. 2 is a bottom view of the suture retainer package with an armed suture stored therein;

FIG. 3 is an exploded perspective view of the suture retainer package with an armed suture stored therein;

FIG. 4. is a top plan view of the base;

FIG. 4a is a detailed sectional side view of the camming wall of the base;

FIG. 5 is a bottom view of the cover;

FIG. 5a is a detailed sectional side view of the camming wall of the cover; and

FIGS. 6, 7, and 8 are sectional side views progressively illustrating the removal of a surgical needle from the suture retainer package.

DETAILED DESCRIPTION OF THE PREFERRED EMBODIMENTS

Figure 1A:
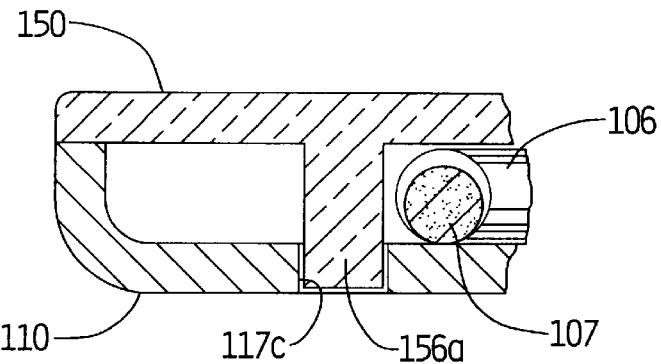
FIG. 1A is a sectional view taken along line 1A—1A in FIG. 1.

As used herein the terms "distal" and "proximal", "above" and "below", "up" and "down", "left" and "right" and similar such terms are used relative to each other and not to an external fixed frame of reference.

Referring to FIGS. 1 and 2, suture retainer package 100 is container for holding and dispensing a needle-suture combination 105, which includes a surgical needle 106 to which suture 107 is attached. Needle 106 is typically curved into an arcuate shape and is typically fabricated from stainless steel. Suture 107 can be monofilament or multifilament, and can be bioabsorbable or non-bioabsorbable. Typical non-bioabsorbable materials from which sutures can be fabricated include nylon and polypropylene. Bioabsorbable materials can be natural materials such as catgut or collagen, or synthetic materials such as polymers of glycolide, lactide, p-dioxanone, ε-caprolactone, trimethylene carbonate, and physical and chemical combinations thereof. Needle and suture diameter can vary according to the intended use. For example, typical sizes for sutures can range from USP Size 12-0 (about 0.001 to about 0.009 mm) to USP Size 10 (about 1.200 to about 1.299 mm). As can be seen from FIG. 1, the suture is stored in the suture retainer package 100 in a looped coil configuration, the loops being shaped approximately as a FIG. 8. The needle 106 is positioned at one end of the suture retainer package 100 and is held in place by a foam pad 140, as discussed below.

The suture retainer package 100 is generally flat and rectangular in shape and includes a base 110 and a cover 150. Generally, the suture retainer package 100 can have a length L ranging from about 3.30 inches to about 4.00 inches and width W ranging from about 1.25 inches to about 1.65 inches. Distal end 103 of the suture retainer package 100 provides an exit for the needled suture, as discussed below.

Base 110 and cover 150 can be fabricated from the same or different synthetic polymers selected from, for example, polypropylene, HDPE, and the like. The synthetic polymer should have sufficient strength, flexibility, and resiliency for the purposes described below and should be medically compatible with the intended purpose of storing surgical needles and sutures. Cover 150 is preferably transparent to allow visualization of the contents of the suture retainer package 100. Cover 150 or base 110 may optionally have attached thereto a sheet of paper or other material (not shown) having indicia printed thereon for identification of the contents of the suture retainer package 100.

Figure 1B:
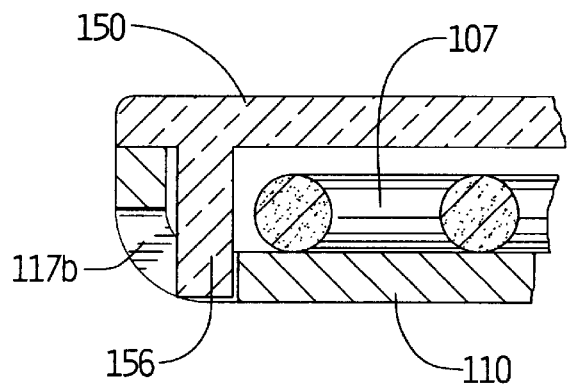
FIG. 1B is a sectional view taken along line 1B—1B in FIG. 1.

Referring additionally now to FIGS. 3, 4, and 4a, base 110 is an integral single piece body 111 having a plurality of winding pin apertures 112, a central orientation pin aperture 113, and an asymmetrically positioned aperture 114 for reception of the tail end of the suture. V-shaped ridges 115, in conjunction with corresponding V-shaped ridges 155 of the cover 150, serve as guides to constrict the center of the suture loops to maintain the coiled suture loops in the desired FIG. 8 configuration. As can be seen from FIGS. 1, 3, and 4, each of the two V-shaped ridges 115 has a vertex portion in opposing relationship to the vertex portion of the other V-shaped ridge so as to define a constricted space therebetween. Base 110 includes a plurality of slots 117 and projections 118 which serve as catches. Slots 117 are adapted to receive latches 158 of the cover 150; catches 118 are adapted to engage corresponding latches 158 to lock together the cover 150 and base 110 with snap lock engagements. Additionally, as shown in FIG. 1B, slots 117b in the base are adapted to engage bosses 156, which project downwardly from the cover 150. The bosses 156 are flat, plate like projections which serve as baffles to prevent the suture from getting snagged or caught in the junction between cover 150 and base 110. As shown in FIG. 1A, in the vicinity of the distal exit of the package end 103, the baffle is preferably a depending cylindrical boss 156a which engages a circular slot 117c to prevent snagging of the suture upon its withdrawal from package 100. Peripheral ridge 119 extends upward around the edge of the base 110 to define an enclosure volume in which the needle-suture combination 105 is stored. Ridge 116 serves as a wall to divide the enclosure volume into a needle storage compartment 101 and a suture storage compartment 102.

In the vicinity of the distal left corner the base includes a lengthwise extending notch 125 across which needle 106 extends. Notch 125 permits the needle to be grasped by a suitable grasping instrument for removal from the suture retainer package 100.

Base 110 includes a longitudinally oriented camming wall 120 extending from end 103 of the suture retainer package 100 and having a proximal inclined camming surface 121. Camming wall 120 is positioned adjacent the left side of slot 117a and catch 118a. Camming surface 121 is adapted to be slidingly engaged by needle 106 as explained below. A longitudinal row of spaced apart indexing studs 123 is positioned along the right side of notch 125. Studs 123 permit the stabilized positioning of the needle 106 at discrete spaced apart intervals in the needle storage compartment 101.

Figure 1C:
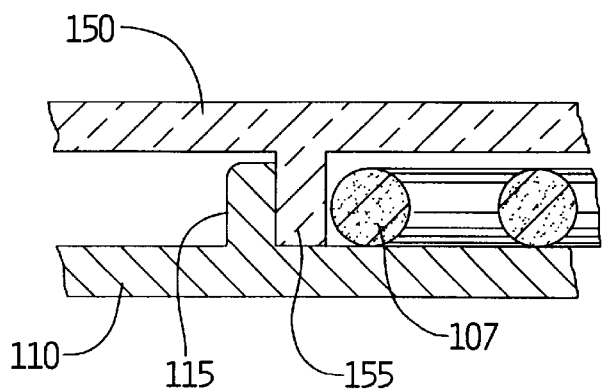
FIG. 1C is a sectional view taken along line 1C—1C in FIG. 1.

Referring now to FIGS. 1, 3, and 5, cover 150 includes an integral single piece body 151 having a cutaway portion 154 at the distal left corner. Downward projecting latches 158 are adapted to engage corresponding slots 117 and/or catches 118 in the base. Particularly, latch 158a is adapted to engage slot 117a and catch 118a in the base. Referring to FIG. 1C, cover 150 further includes V-shaped ridges 155 which, when the cover 150 and base 110 are assembled, are adjacent to corresponding ridges 115 in the base to constrict the center of the suture loop, as mentioned above. The V-shaped ridges 115 and 155 cooperate to prevent the suture from getting caught or snagged in the snap lock engagements. Foam pad 140 can be attached to the underside of cover 150, for example by adhesive, and is positioned to contact needle 106. Foam pad 140 is preferably an open celled polymeric material such as, for example, polyurethane. Foam pad 140 helps to keep needle 106 stably positioned in the suture retainer package 100 until intentionally removed by the surgeon. Alternatively, foam pad 140 can be positioned on base 110 and needle 106 can be secured by being pierced into the foam pad 140 or positioned within a slot in the foam pad 140.

Referring now to FIGS. 1, 3, 5, and 5a, cover 150 includes a longitudinally oriented camming wall 152 extending from end 103 of the suture retainer package 100 and having a proximal inclined camming surface 153. Camming wall 152 is positioned adjacent the right side of latch 158a and slot 157a. Camming surface 153 is adapted to be slidingly engaged by the needle 106 as explained below.

As can be seen now in FIG. 6, needle 106 is secured in a desired storage position within the closed suture retainer package 100 by indexing studs 133 and foam pad 140. The position of the needle along the line of indexing studs can be selected based on, for example, the degree of curvature of the needle. Alternatively, more than one needle-suture combination can be stored in the suture retainer package 100 and multiple needles can be spaced apart in the needle storage chamber 101 at respective indexed locations. Removal of the needle 106 is accomplished by grasping the needle with an appropriate instrument at the portion of the needle extending across notch 105. The needle is then pulled distally.

Referring to FIGS. 7 and 8, distal movement of the needle causes the needle to slidingly engage both camming surface 121 and 153, thereby biasing the distal edge of cover 150 upward and the distal edge of base 110 downward. Thus, latch 158a is disengaged from catch 118a and slot 117a, and the distal end 103 of the suture retainer package is cammed into an open configuration to permit removal of the needle 106 and suture 107 as shown in FIG. 8.

It will be understood that various modifications may be made to the embodiments described herein. Therefore the above description should not be construed as limiting, but merely as exemplifications of preferred embodiments. Those skilled in the art will envision other modifications within the scope and spirit of the claims appended hereto.

What is claimed is:

1. A package for retaining a needle-suture combination, which comprises:
    a) a cover; and
    b) a base which is connected to the cover by snap lock engagement so as to define an enclosure volume, the base having first and second V-shaped ridges, each V-shaped ridge having a vertex portion, the vertex portion of the first V-shaped ridge being in opposing relation to the vertex portion of the second V-shaped ridge so as to define a constricted space therebetween.

2. The package of claim 1 wherein the cover includes third and fourth V-shaped ridges corresponding respectively to the first and second V-shaped ridges of the base and engageable with the first and second V-shaped ridges.

3. The package of claim 1 wherein the base includes a dividing ridge for defining a needle retaining compartment and a suture containing compartment.

4. The package of claim 1 wherein the base further includes a longitudinally oriented row of spaced apart indexing studs.

5. The package of claim 4 wherein the base includes a longitudinally extending notch positioned in the vicinity of the row of indexing studs.

6. The package of claim 5 further including a longitudinally oriented ridge having an inclined camming edge.

7. The package of claim 1 wherein the base includes winding pin access apertures.

8. The package of claim 3 further including a foam pad in the needle retaining compartment.

9. The package of claim 5 wherein the cover includes a cutaway portion in a location corresponding to the longitudinally extending notch in the base so as to define a needle access opening.

10. A packaged needle-suture combination, which comprises:
   a) a cover; and
   b) a base which is connected to the cover by snap lock engagement so as to define an enclosure volume in which is positioned at least one needle-suture combination, the base including first and second V-shaped guides for maintaining a major portion of the suture in a coiled configuration with generally figure 8 shaped loops.

11. The packaged needle-suture combination of claim 1 wherein the first and second V-shaped ridges each have a vertex portion, the vertex portion of the first V-shaped ridge being in opposing relationship to the vertex portion of the second V-shaped ridge.

12. The packaged needle-suture combination of claim 10 wherein the cover includes third and fourth V-shaped ridges corresponding respectively to the first and second V-shaped ridges of the base and engageable with the first and second V-shaped ridges.

13. The packaged needle-suture combination of claim 10 wherein the base includes a dividing ridge for defining a needle retaining compartment and a suture containing compartment, the needle being positioned in the needle-retaining compartment and the major portion of the suture being retained in the suture retaining compartment.

14. The packaged needle suture combination of claim 13 wherein the base further includes a longitudinally oriented row of spaced apart indexing studs positioned in the needle-retaining compartment, the needle being positioned between two of said indexing studs.

15. The packaged needle-suture combination of claim 14 wherein the base includes a longitudinally extending notch positioned in the vicinity of the row of indexing studs.

16. The packaged needle-suture combination of claim 15 further including a longitudinally oriented ridge having an inclined camming edge, said ridge causing an end of the base to separate from a corresponding end of the cover so as to create an opening for withdrawal of the needle suture combination in response to contacting of the inclined camming edge with the needle.

17. The packaged needle-suture combination of claim 10 wherein the base includes a plurality of winding pin access apertures.

18. The packaged needle-suture combination of claim 13 further including a foam pad in the needle retaining compartment.

19. The packaged needle-suture combination of claim 15 wherein the cover includes a cutaway portion in a location corresponding to the longitudinally extending notch in the base so as to define a needle access opening.

20. The packaged needle-suture combination of claim 10 wherein both the base and the cover are fabricated from a synthetic polymeric material.

* * * * *